United States Patent
Voisin et al.

(10) Patent No.: US 10,449,134 B2
(45) Date of Patent: Oct. 22, 2019

(54) PROCESS FOR TREATING KERATIN FIBRES WITH A COMPOSITION COMPRISING AN AMINO ACID

(71) Applicant: L'OREAL, Paris (FR)

(72) Inventors: Sebastien Voisin, Levallois Perret (FR); Gregory Plos, Paris (FR)

(73) Assignee: L'OREAL, Paris (FR)

( * ) Notice: Subject to any disclaimer, the term of this patent is extended or adjusted under 35 U.S.C. 154(b) by 56 days.

(21) Appl. No.: 15/537,958

(22) PCT Filed: Dec. 22, 2015

(86) PCT No.: PCT/EP2015/080936
§ 371 (c)(1),
(2) Date: Jun. 20, 2017

(87) PCT Pub. No.: WO2016/102543
PCT Pub. Date: Jun. 30, 2016

(65) Prior Publication Data
US 2018/0042831 A1    Feb. 15, 2018

(30) Foreign Application Priority Data
Dec. 23, 2014    (FR) .................................... 14 63221

(51) Int. Cl.
| | | |
|---|---|---|
| A61K 8/41 | (2006.01) | |
| A61Q 5/04 | (2006.01) | |
| A61K 8/44 | (2006.01) | |
| A61K 8/42 | (2006.01) | |
| A61K 8/73 | (2006.01) | |
| A61K 8/898 | (2006.01) | |
| A45D 7/06 | (2006.01) | |

(52) U.S. Cl.
CPC ............... *A61K 8/447* (2013.01); *A45D 7/06* (2013.01); *A61K 8/41* (2013.01); *A61K 8/42* (2013.01); *A61K 8/44* (2013.01); *A61K 8/731* (2013.01); *A61K 8/898* (2013.01); *A61Q 5/04* (2013.01)

(58) Field of Classification Search
None
See application file for complete search history.

(56) References Cited

U.S. PATENT DOCUMENTS

| | | | |
|---|---|---|---|
| 5,932,201 | A | 8/1999 | de Labbey et al. |
| 8,906,352 | B2 | 12/2014 | Malle et al. |
| 2012/0121526 | A1 | 5/2012 | Hohenstein et al. |
| 2012/0230935 | A1 | 9/2012 | Kim et al. |
| 2012/0260934 | A1* | 10/2012 | Schweinsberg ........ A61K 8/585 132/203 |

FOREIGN PATENT DOCUMENTS

| | | |
|---|---|---|
| EP | 0173109 A2 | 3/1986 |
| EP | 1837010 A2 | 9/2007 |
| WO | 2007/135299 A1 | 11/2007 |
| WO | 2009/117344 A2 | 9/2009 |
| WO | 2010/049434 A2 | 5/2010 |
| WO | 2011/104282 A2 | 9/2011 |
| WO | 2012/027369 A2 | 3/2012 |

OTHER PUBLICATIONS

International Search Report for PCT/EP2015/80936, dated Mar. 8, 2016.
Gordon, Julius A. et al., "The Relationship of Structure to the Effectiveness of Denaturing Agents for Proteins," Denaturants of Proteins, Department of Biochemistry, vol. 2, No. 1, Jan.-Feb. 1963, pp. 47-57.

* cited by examiner

*Primary Examiner* — Susan T Tran
(74) *Attorney, Agent, or Firm* — The Marbury Law Group, PLLC

(57) ABSTRACT

The present invention relates to a process for treating keratin fibers, in particular the hair, comprising:
a) the application, to said fibers, of a composition having a pH greater than or equal to 8, at 25° C., and comprising at least one amino acid chosen from those of formulae (I) and (II) below, and also the betaine forms thereof, the optical isomers thereof, the solvates thereof such as the hydrates, and the organic or inorganic base or acid salts thereof: in which formulae (I) and (II):
R represents a hydrogen atom, or a linear or branched, preferably linear, $C_1$-$C_5$ alkyl group, said alkyl group being optionally substituted with at least one group chosen from hydroxyl, —C(O)—OH, —S(O)$_2$—OH, —C(O)—O$^-$, M$^+$, and —S(O)$_2$—O$^-$, M$^+$, with M$^+$ representing a cationic counterion such as an alkali metal, alkaline-earth metal, or ammonium,
n is 0 or 1;
b) followed by a step of straightening/relaxing the keratin fibers by means of a straightening iron at a temperature of at least 100° C.

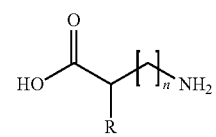

(I)

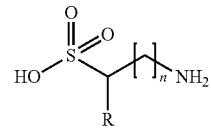

(II)

19 Claims, No Drawings

PROCESS FOR TREATING KERATIN FIBRES WITH A COMPOSITION COMPRISING AN AMINO ACID

CROSS REFERENCE TO RELATED APPLICATIONS

This is a national stage application of PCT/EP2015/080936, filed internationally on Dec. 22, 2015, which claims priority to French Application No. 1463221, filed on Dec. 23, 2014, both of which are incorporated by reference herein in their entireties.

The present invention relates to a process for treating keratin fibres, in particular the hair, comprising the application of a composition comprising at least one specific amino acid and a step of straightening/relaxing by means of a straightening iron.

In the hair field, consumers wish to have available compositions which make it possible to introduce a temporary change to their head of hair, while targeting good persistence of the effect produced. In general, it is desired for the change to withstand shampooing for at least fifteen days or even more, depending on the nature of said change.

Heat treatments are generally used to modify the shape of the head of hair in a long-lasting manner. These treatments allow a visual modification of the appearance of the hairstyle, combining a decrease in the degree of frizziness, a reduction in overall volume of the head of hair, a decrease in little curls, a gain in manageability, a straighter visual appearance, a substantial gain in sheen, and a resistance to humidity and to heat in order to maintain the hairstyle throughout the day.

Moreover, this type of treatment has the advantage of facilitating the daily maintenance of the head of hair, with the use of fewer care products, in particular rinse-out care products such as conditioners or masks, or leave-in care products such as sera, care creams or balms, or mousses for generating manageability. Drying of the hair is facilitated, with a much shortened blow-drying time and a decrease in the daily use of flat tongs, in terms of both time and strength. This thus makes it possible to limit the risks of damaging the hair through combined factors of mechanical and thermal stress.

Several techniques are combined with these heat treatments. A first technique is based on the use of compositions based on thiol-based reducing agents. These techniques require rigorous observation of the application conditions recommended by the suppliers, in particular in terms of amount and leave-in time. In addition, they may be contraindicated on hair that is too sensitized and may not be compatible with the same-day application of other treatments, such as dyeing or bleaching operations. Moreover, they have an unpleasant smell.

Another technique is based on the use of compositions based on formol (or formaldehyde) and derivatives thereof. These treatments have the particularity of being robust, perfectly compatible with all the other conventional hair treatments, such as the thiol-based straightening operations previously mentioned, alkaline relaxing operations, dyeing or bleaching operations of all types, carried out before or after. They provide the hair with excellent manageability, a very bright sheen and easy daily care. However, in the event of repeated applications, further damage to the hair occurs, which can lead to breaking of the hairs. Furthermore, for toxicological reasons, the use of some of these compounds is now prohibited and/or regulated. It is therefore increasingly sought to avoid the use of such substances, which may prove to be aggressive to the hair and other keratin materials.

Another technique is based on the use of compositions based on acids, and quite particularly on the use of glyoxylic acid. Patent application WO 2011/104 282 thus proposed a novel process for semi-permanently straightening the hair, which consists in applying an α-keto acid solution to the hair for 15 to 120 minutes, then drying and, finally, straightening the head of hair with an iron at a temperature of about 200° C. The α-keto acid employed is preferably glyoxylic acid.

However, it has been noted that glyoxylic acid may not be well tolerated, in particular when the scalp is sensitive and/or irritated. Its volatility, amplified by the use of heat from the iron, can also be a problem. Furthermore, the compositions of the prior art may impair the hair and/or impair its colour.

Treatments using a composition comprising a base combined with a heat treatment have also been proposed for straightening the hair. Such treatments make it possible to obtain good relaxing of curls, but can lead to modifications of the hair fibre. Document EP 1 837 010 describes in particular a straightening/relaxing process using a composition comprising sodium hydroxide and a heat treatment. Document WO 2007/144707 describes a straightening/relaxing process using a composition comprising a non-hydroxylated base such as monoethanolamine or ethylenediamine, combined with a heat treatment. Document WO 2009/117344 also describes a straightening/relaxing process using a composition comprising a non-hydroxylated base and a protein-denaturing agent, combined with a heat treatment.

In order to limit hair fibre modifications, it has also been proposed to use compositions comprising weak acids at alkaline pH, combined with a heat treatment. Document WO 2010/049434 describes, for example, a straightening/relaxing process in which a composition comprising a dicarboxylic acid, such as maleic acid, and heat treatment are applied.

There is still a need to develop a process for treating the hair, in particular a straightening/relaxing process which makes it possible to straighten/relax and/or reduce the frizziness of the hair in an effective and long-lasting manner while limiting the degradation of the hair.

The applicant has now discovered that the use of a composition having a pH greater than or equal to 8 and comprising at least one specific amino acid combined with a step of straightening with a straightening iron at a temperature of at least 100° C. makes it possible to achieve the desired long-lasting straightening properties.

Thus, a subject of the present invention is a process for treating keratin fibres, in particular the hair, comprising a) the application, to the keratin fibres, of a composition having a pH greater than or equal to 8, at 25° C., and comprising at least one amino acid chosen from those of formulae (I) and (II) below, and also the betaine forms thereof, the optical isomers thereof, the solvates thereof such as the hydrates, and the organic or inorganic acid or base salts thereof:

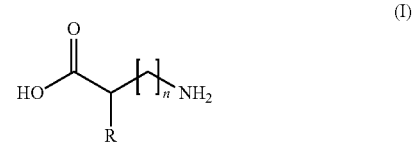

(I)

-continued (II)
$$HO-\overset{\overset{O}{\|}}{\underset{\|}{S}}-\overset{R}{\underset{|}{C}H}-(CH_2)_n-NH_2$$

in which formulae (I) and (II):
R represents a hydrogen atom, or a linear or branched, preferably linear, $C_1$-$C_5$ alkyl group, said alkyl group being optionally substituted with at least one group chosen from hydroxyl, —C(O)—OH, —S(O)$_2$—OH, —C(O)—O$^-$, M$^+$, and —S(O)$_2$—O$^-$, M$^+$, with M$^+$ representing a cationic counterion such as an alkali metal, alkaline-earth metal, or ammonium,
n is 0 or 1;

b) followed by a step of straightening/relaxing the keratin fibres by means of a straightening iron at a temperature of at least 100° C.

The process of the invention makes it possible in particular to obtain good long-lasting relaxation of curls, while limiting the degradation of the hair.

Preferably, the process according to the invention does not comprise a step of applying a reducing composition comprising a reducing agent.

Other characteristics and advantages of the invention will emerge more clearly on reading the description and the examples that follow.

In that which follows, the expression "at least one" is equivalent to the expression "one or more".

As previously indicated, the process for treating keratin fibres according to the invention comprises a) a step of application, to the keratin fibres, of a composition comprising at least one amino acid chosen from those of formulae (I) and (II) below, and also the betaine forms thereof, the optical isomers thereof, the solvates thereof such as the hydrates, and the organic or inorganic acid or base salts thereof:

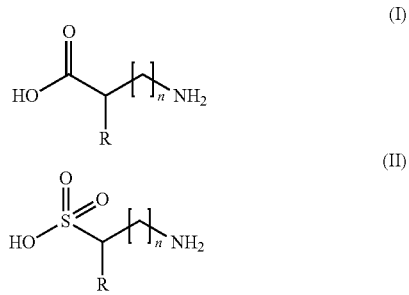

(I)

(II)

in which formulae (I) and (II):
R represents a hydrogen atom, or a linear or branched, preferably linear, $C_1$-$C_5$ alkyl group, said alkyl group being optionally substituted with at least one group chosen from hydroxyl, —C(O)—OH, —S(O)$_2$—OH, —C(O)—O$^-$, M$^+$, and —S(O)$_2$—O$^-$, M$^+$, with M$^+$ representing a cationic counterion such as an alkali metal, alkaline-earth metal, or ammonium,
n is 0 or 1.

In the composition containing them, the amino acid(s) may be in their non-ionized form (I) or (II) or in their ionized or betaine form (I') or (II'):

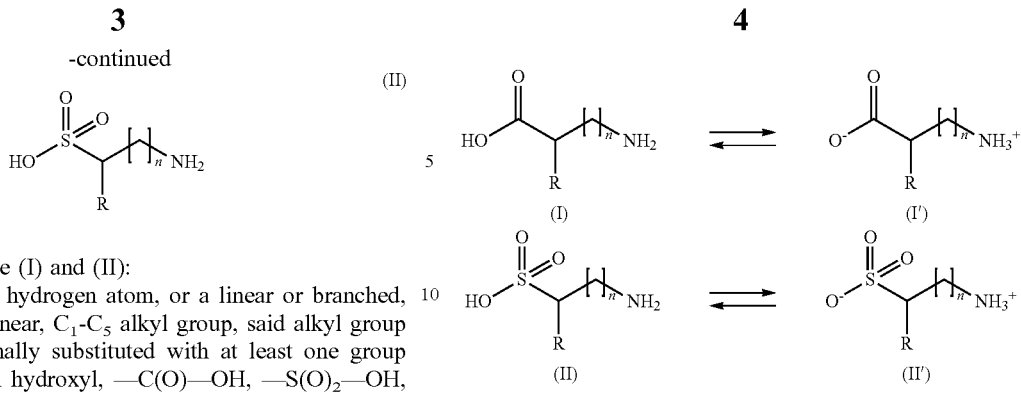

in which formulae R represents a hydrogen atom, or a linear or branched $C_1$-$C_5$ alkyl group, optionally substituted with a hydroxyl group, or a carboxylate group, and n is 0 or 1.

The amino acid(s) of the invention is (are) preferably chosen from "neutral" or "acidic" amino acids. The term "neutral amino acids" is intended to mean amino acids which have a pH, at ambient temperature (25° C.), in water of inclusively between 5 and 7. The term "acidic amino acids" is intended to mean amino acids which have a pH, at ambient temperature, in water of less than 5.

Preferably, the amino acids of the invention comprise a number of amino groups less than or equal to the number of acid groups.

More preferably, the amino acid(s) is (are) chosen from the amino acids of formula (I).

The amino acid(s) or the salt(s) thereof is (are) preferentially chosen from glycine, alanine, serine, beta-alanine and taurine, sodium glycinate, sodium alaninate, sodium serinate, lithium beta-alaninate and sodium taurate, preferably glycine.

The amino acid(s) is (are) present in the composition in a content ranging from 1.5% to 15% by weight and preferably from 2% to 10% by weight relative to the total weight of the composition.

The composition used in the process of the invention may comprise at least one basifying agent or one acidifying agent.

The basifying agent(s) may be chosen from inorganic or organic alkaline agents.

In particular, the basifying agent(s) may be chosen from sodium hydroxide, potassium hydroxide, lithium hydroxide, calcium hydroxide, magnesium hydroxide and the conjugated bases of formulae (Ib) and (IIb), below, of the amino acid of formula (I) or (II):

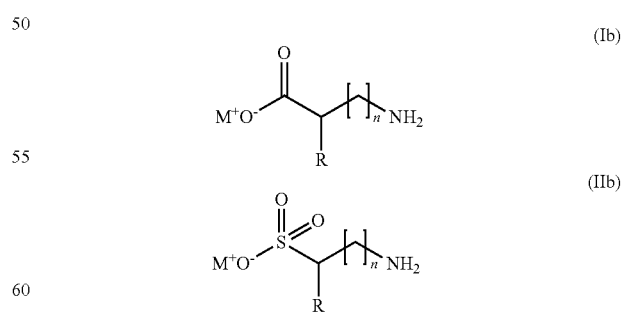

in which formulae (Ib) and (IIb) R, n and M$^+$ are as previously defined.

According to one particular embodiment, the basifying agent(s) is (are) chosen from sodium hydroxide and potassium hydroxide, preferably sodium hydroxide.

According to another particular embodiment, the basifying agent(s) is (are) chosen from the conjugated bases of formulae (Ib) and (IIb) of the amino acid of formula (I) or (II).

When it (they) is (are) present, the basifying agent(s) is (are) present in the composition in a content ranging from 1.5% to 15% by weight and preferably from 2% to 10% by weight relative to the total weight of the composition.

The acidifying agent(s) may be chosen from inorganic or organic acids.

The inorganic acid may be chosen from hydrochloric acid, sulfuric acid and orthophosphoric acid. Preferably, the inorganic acid may be chosen from hydrochloric acid and orthophosphoric acid.

The organic acid may be chosen from hydroxy acids, in particular from citric acid, lactic acid, glycolic acid, gluconic acid, tartaric acid and malic acid, and more preferably from lactic acid and glycolic acid.

When it (they) is (are) present, the acidifying agent(s) is (are) present in the composition in a content ranging from 1.5% to 15% by weight and preferably from 2% to 10% by weight relative to the total weight of the composition.

According to one particular embodiment, the composition used in the process of the invention comprises:
an amino acid chosen from the amino acids of formulae (I) and (II),
and the conjugated base of formula (Ib) or (IIb) of said amino acid.

According to one preferred embodiment, the molar ratio of amino acid of formula (I) or (II) to its conjugated base (Ib) or (IIb) ranges from 1 to 100 and preferably from 1 to 10.

Preferably, the composition comprises an amino acid of formula (I) and its conjugated base of formula (Ib).

According to one particularly preferred embodiment, the composition comprises glycine and sodium glycinate, preferably according to a glycine/glycinate molar ratio ranging from 1 to 100 and preferably from 1 to 10.

The composition used in the process according to the invention may also comprise one or more amino denaturing agents.

The term "denaturing agent" is intended to mean an organic or inorganic compound which has both at least one electron donor site of basic or nucleophilic nature and at least one electron acceptor site of acidic or electrophilic nature, interacting with the weak bonds of the keratin.

According to the invention, a denaturing agent is a compound capable of reducing the optical rotation of a model protein, such as, for example, bovine serum albumin, by at least 7° and/or 5° at 579 nm, the measurements being carried out after 3 hours of incubation at 37° C., using a polarimeter, as described in Biochemistry 2 (1), 47-57, 1963:
either in a 0.05 M Tris buffer, pH 7.6,
or in a 5.45 M urea solution when the solubility of the compound is insufficient in the 0.05 M Tris buffer, pH 7.6.

The compound is considered to be a denaturing agent according to the invention if the decrease in the optical rotation is by at least 7° in the 0.05 M Tris buffer, pH 7.6, and/or by at least 5° in the 5.45 M urea solution.

Preferably, the amino denaturing agent is chosen from ureas and/or urea derivatives and guanidines.

The term "urea derivative" is intended to mean any compound other than urea CO(NH$_2$)$_2$ itself, comprising in its chemical formula a carbonyl group covalently bonded via two single bonds a to two nitrogen atoms, i.e. a unit

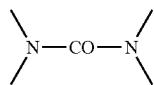

Preferably, the denaturing agent is chosen from the compounds of formula (III) or (IV), the salts thereof or the hydrates thereof:

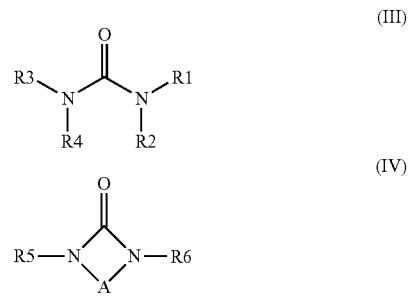

in which:
R1, R2, R3 and R4 represent, independently:
(i) a hydrogen atom or
(ii) a linear or branched, cyclic or acyclic $C_1$-$C_5$ lower alkyl or alkenyl radical, a $C_1$-$C_5$ alkoxy radical, a $C_6$-$C_{18}$ aryl radical, a 5- to 8-membered heterocyclic radical; these radicals being optionally substituted with a radical chosen from the following radicals: hydroxyl, ($C_1$-$C_4$)alkyl, (di)($C_1$-$C_4$)(alkyl)amino such as dimethylamino, carboxyl, halogen, $C_6$-$C_{18}$ aryl, carboxamide and N-methylcarboxamide;
it being understood that:
when R1, R2 and R3 represent a hydrogen atom, R4 may denote a carboxamide, methoxy, ethoxy, 1,2,4-triazolyl, cyclopentyl, ($C_1$-$C_6$)alkylcarbonyl such as acetyl, or ($C_1$-$C_6$)alkoxycarbonyl such as methoxycarbonyl or ethoxycarbonyl radical, —C(O)—CH═CH—C(O)—OH, phenyl optionally substituted with a chlorine atom or a hydroxyl, benzyl or 2,5-dioxo-4-imidazolidinyl radical;
when R1 and R3 represent a hydrogen atom, R2 may represent a hydrogen atom or a methyl or ethyl radical and R4 may represent an acetyl radical;
when R1=R2=H, R3 and R4 can form, with the nitrogen atom that bears them, a piperidine, 3-methylpyrazole, 3,5-dimethylpyrazole or maleimide ring;
R1 and R2 and also R3 and R4 can form, with the nitrogen atom that bears them, an imidazole ring;
R5 and R6 represent, independently of each other:
(iii) a hydrogen atom or
(iv) a linear or branched, cyclic or acyclic $C_1$-$C_5$ lower alkyl, acyl or alkenyl radical, a $C_1$-$C_5$ alkoxy radical, a $C_6$-$C_{18}$ aryl radical, a 5- to 8-membered heterocyclic radical; these radicals being optionally substituted with a radical chosen from the following radicals: hydroxyl, amino, dimethylamino, carboxyl, halogen, $C_6$-$C_{18}$ aryl, carboxamide and N-methylcarboxamide;
A is a radical chosen from the following radicals: CH$_2$—CH$_2$, CH═CH, CH$_2$—C(O), C(O)—NH, CH═N, C(O)—C(O), CH(OH)—CH(OH), (HO(O)C)CH—CH, CH(OH)—C(O), CH$_2$—CH$_2$—CH$_2$, CH$_2$—NH—C(O), CH═C(CH$_3$)—C(O), NH—C(O)—NH, CH$_2$—CH$_2$—C(O), CH$_2$—N(CH$_3$)—

CH$_2$, NH—CH$_2$—NH, C(O)—CH(CH$_3$)—CH$_2$, C(O)—CH$_2$—C(O), C(O)—NH—C(O), C(O)—CH(C(O)OH)—CH$_2$, C(O)—CH=C(C(O)OH), C(O)—CH=C(CH$_3$), C(O)—C(NH$_2$)=CH, C(O)—C(CH$_3$)=N, C(O)—CH=CH, C(O)—CH=N and C(O)—N=CH.

Among the compounds of formula (III) that are particularly preferred according to the invention, mention may be made of:

urea
methylurea
ethylurea
propylurea
n-butylurea
sec-butylurea
isobutylurea
tert-butylurea
cyclopentylurea
ethoxyurea
hydroxyethylurea
N-(2-hydroxypropyl)urea
N-(3-hydroxypropyl)urea
N-(2-dimethylaminopropyl)urea
N-(3-dimethylaminopropyl)urea
1-(3-hydroxyphenyl)urea
benzylurea
N-carbamoylmaleamide
N-carbamoylmaleamic acid
piperidinecarboxamide
1,2,4-triazol-4-ylurea
hydantoic acid
methyl allophanate
ethyl allophanate
acetylurea
hydroxyethyleneurea
2-(hydroxyethyl)ethyleneurea
diallylurea
chloroethylurea
N,N-dimethylurea
N,N-diethylurea
N,N-dipropylurea
cyclopentyl-1-methylurea
1,3-dimethylurea
1,3-diethylurea
1,3-bis(2-hydroxyethyl)urea
1,3-bis(2-hydroxypropyl)urea
1,3-bis(3-hydroxypropyl)urea
1,3-dipropylurea
ethyl-3-propylurea
sec-butyl-3-methylurea
isobutyl-3-methylurea
cyclopentyl-3-methylurea
N-acetyl-N'-methylurea
trimethylurea
butyl-3,3-dimethylurea
tetramethylurea and
benzylurea.

Among the compounds of formula (IV) that are particularly preferred according to the invention, mention may be made of:

parabanic acid
1,2-dihydro-3H-1,2,4-triazol-2-one
barbituric acid
uracil
1-methyluracil
3-methyluracil
5-methyluracil
1,3-dimethyluracil
5-azauracil
6-azauracil
5-fluorouracil
6-fluorouracil
1,3-dimethyl-5-fluorouracil
5-aminouracil
6-aminouracil
6-amino-1-methyluracil
6-amino-1,3-dimethyluracil
4-chlorouracil
5-chlorouracil
5,6-dihydrouracil
5,6-dihydro-5-methyluracil
2-imidazolidone
1-methyl-2-imidazolidinone
1,3-dimethyl-2-imidazolidinone
4,5-dihydroxy-imidazolidin-2-one
1-(2-hydroxyethyl)-2-imidazolidinone
1-(2-hydroxypropyl)-2-imidazolidinone
1-(3-hydroxypropyl)-2-imidazolidinone
4,5-dihydroxy-1,3-dimethylimidazolidin-2-one
1,3-bis(2-hydroxyethyl)-2-imidazolidinone
2-imidazolidone-4-carboxylic acid
1-(2-aminoethyl)-2-imidazole
4-methyl-1,2,4-triazoline-3,5-dione
2,4-dihydroxy-6-methylpyrimidine
1-amino-4,5-dihydro-1H-tetrazol-5-one
hydantoin
1-methylhydantoin
5-methylhydantoin
5,5-dimethylhydantoin
5-ethylhydantoin
5-n-propylhydantoin
5-ethyl-5-methylhydantoin
5-hydroxy-5-methylhydantoin
5-hydroxymethylhydantoin
1-allylhydantoin
1-aminohydantoin
hydantoin-5-acetic acid
4-amino-1,2,4-triazolone-3,5-dione
hexahydro-1,2,4,5-tetrazine-3,6-dione
5-methyl-1,3,5-triazinon-2-one
1-methyltetrahydropyrimidin-2-one
2,4-dioxohexahydro-1,3,5-triazine
urazole
4-methylurazole
orotic acid
dihydroxyorotic acid
2,4,5-trihydroxypyrimidine
2-hydroxy-4-methylpyrimidine
4,5-diamino-2,6-dihydroxypyrimidine
barbituric acid
1,3-dimethylbarbituric acid
cyanuric acid
1-methyl-hexahydropyrimidine-2,4-dione
1,3-dimethyl-3,4,5,6-tetrahydro-2-1H-pyrimidinone
5-(hydroxymethyl)-2,4-(1H,3H)-pyrimidinedione
2,4-dihydroxypyrimidine-5-carboxylic acid
6-azathymine
5-methyl-1,3,5-triazinan-2-one
N-carbamoylmaleamic acid and
alloxan monohydrate.

Preferentially, said denaturing agent(s) is (are) chosen from urea, alkylurea and hydroxyalkylurea, in particular hydroxyethylurea, even more preferably from urea and hydroxyethylurea.

The term "guanidine" is intended to mean any derivative comprising in its chemical formula at least one carbon atom double-bonded to a nitrogen atom and single-bonded to two other nitrogen atoms. These guanidines are more particularly selected from the compounds of general formula (V) below, and the organic or inorganic salts thereof:

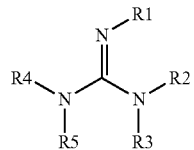
(V)

in which:
R1, R2, R3, R4 and R5 represent, independently:
(i) a hydrogen atom or
(ii) a linear or branched $C_1$-$C_4$ alkyl or alkenyl radical, optionally substituted with one or 2 radicals chosen from: hydroxyl, amino, dimethylamino, methoxy, ethoxy, carboxyl, carboxamide, N-methylcarboxamide or $SO_3H$.

When R1, R2 and R3 and R4 represent a hydrogen atom, R5 may also denote one of the following radicals: acetyl; chloroacetyl; carboxamide; methoxy; ethoxy; 1,2,4-triazolyl; cyclopentyl; methoxycarbonyl; ethoxycarbonyl; C(O)—CH=CH—C(O)OH; phenyl optionally substituted with a chlorine atom or a hydroxyl radical; benzyl; thiazolidone; benzimidazole; benzoxazole; benzothiazole; or C(=NH)—NR6R7 in which R6 and R7 denote, independently of one another, a hydrogen atom or a linear or branched lower $C_1$-$C_4$ alkyl radical optionally substituted with one or 2 radicals chosen from: hydroxyl, amino, dimethylamino, carboxyl or carboxamide; or N-methylcarboxamide; or else a phenyl radical.

When R1=R2=R3=H, R4 and R5 may also form, with the nitrogen atom which bears them, a pyrrolidine, piperidine, pyrazole or 1,2,4-triazole ring optionally substituted with 1 or 2 radicals chosen from: hydroxyl, amino or carboxyl.

When R1=R2=H, and R4=H or methyl, R3 and R5 may also together form a 5-membered ring optionally containing an oxo group.

Among the compounds of formula (V), mention may in particular be made of the following preferred compounds:
guanidine hydrochloride
guanidine acetate
guanidine sulfate
guanidine carbonate
guanidine bicarbonate
guanidine phosphate
guanidine sulfamate
aminoguanidine
aminoguanidine hydrochloride
aminoguanidine sulfate
aminoguanidine bicarbonate
1,3-diaminoguanidine hydrochloride
1-acetylguanidine
chloroacetylguanidine hydrochloride
guanylurea
guanylurea phosphate
phenylguanidine carbonate
phenylguanidine bicarbonate
1-methylguanidine hydrochloride
1,1-dimethylguanidine hydrochloride
1-ethylguanidine hydrochloride
1,1-diethylguanidine hydrochloride
creatine
creatine monohydrate
creatinine hydrochloride
agmatine
agmatine sulfate
guanidinoacetic acid
guanidinosuccinic acid
3-guanidinopropionic acid
4-guanidinobutyric acid
5-guanidinovaleric acid
beta-N-methylguanidinopropionic acid
N-methylguanidinopropionic acid
N-(2-hydroxyethyl)guanidine
N-(3-hydroxypropyl)guanidine
biguanide hydrochloride
N-methylbiguanide hydrochloride
N-ethylbiguanide hydrochloride
N-propylbiguanide hydrochloride
N-butylbiguanide hydrochloride
1,1-dimethylbiguanide hydrochloride
1-phenylbiguanide
1,1,3,3-tetramethylguanidine hydrochloride
2-tert-butyl-1,1,3,3-tetramethylguanidine hydrochloride
L-arginine
D-arginine
DL-arginine
arginic acid
N-amidino-N-(2,3-dihydroxypropyl)glycine
N-amidinotaurine
2-imino-1-imidazolidineacetic acid
1-(2,2-diethoxyethyl)guanidine
1H-pyrazole-1-carboxamidine hydrochloride
5-hydroxy-3-methyl-1H-pyrazole-1-carboximidamide
3,5-diamino-1H-1,2,4-triazole-1-carboximidamide hydrochloride
2-guanidone-4-thiazolidone
2-guanidinobenzimidazole
2-guanidinobenzoxazole
2-guanidinobenzothiazole
pyrrolidinoformamidine hydrochloride.

Among the compounds of formula (V), mention may in particular be made of the following particularly preferred compounds:
guanidine hydrochloride
guanidine acetate
guanidine sulfate
guanidine carbonate
guanidine bicarbonate
guanidine phosphate
guanidine sulfamate
aminoguanidine hydrochloride
aminoguanidine sulfate
aminoguanidine bicarbonate
1,3-diaminoguanidine hydrochloride
guanylurea phosphate
1-methylguanidine hydrochloride
1,1-dimethylguanidine hydrochloride
1-ethylguanidine hydrochloride
creatine monohydrate
creatinine hydrochloride
agmatine
agmatine sulfate
guanidinoacetic acid
guanidinosuccinic acid
3-guanidinopropionic acid
beta-N-methylguanidinopropionic acid N-methylguanidinopropionic acid
N-(2-hydroxyethyl)guanidine
N-(3-hydroxypropyl)guanidine
biguanide hydrochloride
N-methylbiguanide hydrochloride
N-ethylbiguanide hydrochloride
1,1-dimethylbiguanide hydrochloride
1,1,3,3-tetramethylguanidine hydrochloride
2-tert-butyl-1,1,3,3-tetramethylguanidine hydrochloride
L-arginine
DL-arginine
arginic acid
N-amidino-N-(2,3-dihydroxypropyl)glycine
N-amidinotaurine
2-imino-1-imidazolidineacetic acid
1H-pyrazole-1-carboxamidine hydrochloride
3,5-diamino-1H-1,2,4-triazole-1-carboximidamide hydrochloride
2-guanidone-4-thiazolidone.

Preferably, the composition comprises an amino denaturing agent chosen from guanidine, urea, alkylurea, hydroxyalkylurea, in particular hydroxyethylurea, even more preferably from urea and hydroxyethylurea.

When it (they) is (are) present, the denaturing agent(s) is (are) present in an amount ranging from 1% to 30% by weight and preferably from 2% to 25% by weight relative to the total weight of the composition.

The composition according to the invention may likewise also comprise one or more thickeners.

For the purposes of the present invention, the term "thickener" is intended to mean an agent which, by virtue of its presence in the composition, makes it possible to increase the viscosity of said composition by at least 10 cPs and preferably by at least 200 cPs, at 25° C. and at a shear rate of 1 s$^{-1}$. This viscosity may be measured using a cone/plate viscometer (Haake R600 rheometer or the like).

The thickener(s) may be chosen from fatty acid amides obtained from $C_{10}$-$C_{30}$ carboxylic acid (monoisopropanolamide, diethanolamide or monoethanolamide of coconut acids, monoethanolamide of ethoxylated carboxylic alkyl ether acid), polymeric thickeners and in particular polysaccharides, in particular the cellulose-based polymers as described below, gum arabic, gums of microbial origin (scleroglucan gum), crosslinked or non-crosslinked homopolymers and copolymers based on acrylic acid, methacrylic acid or acrylamidopropanesulfonic acid, and the associative polymers as described below, and mixtures thereof.

According to the invention, the term "cellulose-based" polymer is intended to mean any polysaccharide compound bearing in its structure sequences of glucose residues linked via β-1,4 bonds; besides unsubstituted celluloses, the cellulose derivatives may be anionic, cationic, amphoteric or non-ionic. Thus, the cellulose-based polymers of the invention may be chosen from unsubstituted celluloses, including those in a microcrystalline form, and cellulose ethers. Among these cellulose-based polymers, cellulose ethers, cellulose esters and cellulose ester ethers are distinguished. Among the cellulose ethers are ($C_1$-$C_6$) alkylcelluloses and in particular methylhydroxyethylcelluloses. Among the cellulose esters are inorganic esters of cellulose (cellulose nitrates, sulfates, phosphates, etc.), organic esters of cellulose (cellulose monoacetates, triacetates, amidopropionates, acetatebutyrates, acetatepropionates and acetatetrimellitates, etc.), and mixed organic/inorganic esters of cellulose, such as cellulose acetatebutyrate sulfates and cellulose acetatepropionate sulfates. Among the cellulose ester ethers, mention may be made of hydroxypropylmethylcellulose phthalates and ethylcellulose sulfates.

Preferably, the cellulose-based polymer is chosen from ($C_1$-$C_6$) alkylcelluloses and in particular methylhydroxyethylcelluloses.

The associative polymer(s) that may be used according to the invention is (are) water-soluble polymers that are capable, in an aqueous medium, of reversibly combining with each other or with other molecules.

Their chemical structure comprises hydrophilic zones, and hydrophobic zones characterized by at least one fatty chain comprising preferably from 10 to 30 carbon atoms.

The associative polymer(s) that may be used according to the invention may be of anionic, cationic, amphoteric or non-ionic type, such as the polymers sold under the names Pemulen TR1 or TR2 by the company Goodrich (INCI: Acrylates/C10-30 Alkyl Acrylate Crosspolymer), Salcare SC90 by the company Ciba, Aculyn 22, 28, 33, 44 or 46 by the company Röhm & Haas and Elfacos T210 and T212 by the company Akzo.

Among all the thickeners mentioned, the thickener(s) is (are) preferably chosen from polymers, better still from polysaccharides, even better still from cellulose-based polymers, in particular from ($C_1$-$C_6$) alkylcelluloses and in particular methylhydroxyethylcelluloses.

When they are present, the thickeners are present in an amount ranging from 0.01% to 10% by weight, preferably from 0.1% to 5% by weight and preferentially from 0.2% to 3% by weight, relative to the total weight of the composition. The composition used in the process according to the invention may also comprise one or more silicones, and in particular one or more amino silicones.

The term "amino silicone" denotes any silicone comprising at least one primary, secondary or tertiary amine or a quaternary ammonium group.

As amino silicone that can be used in the context of the invention, mention may be made of polysiloxanes, trimethylsilylamodimethicones, and the amino silicones provided by the company Wacker under the name Belsil® ADM 652 or under the name Fluid WR 1300®. Use may also be made of amino silicones in oil-in-water emulsion form, for instance the amino silicone microemulsions provided under the names Finish CT 96 E® or SLM 28020® (Belsil ADM Log 1®) by the company Wacker. Mention will also be made of DC2-8566 Amino Fluid from Dow Corning, or else quaternary ammonium silicones, and multiblock polyoxyalkylenated amino silicones, for instance those sold under the names Silsoft A-843 or Silsoft A+ by Momentive.

When it (they) is (are) present, the amino silicone(s) is (are) present in an amount ranging from 0.01% to 10% by weight, preferably from 0.1% to 5% by weight and preferentially from 0.2% to 3% by weight, relative to the total weight of the composition.

The pH of the composition used in the process of the invention is greater than or equal to 8. Preferably, the pH of the composition ranges from 8 to 12 and more preferably from 9 to 11.

Preferably, the pH of the composition is at less than two units from the pKa relating to the equilibrium of the amino acid of formula (I) or (II) with its base (Ib) or (IIb).

The composition used in the process of the invention may be aqueous or anhydrous. It is preferably aqueous and then comprises water at a concentration ranging from 10% to 99%, better still from 30% to 99% and even better still from 50% to 98% by weight relative to the total weight of the composition.

The composition may in particular comprise one or more organic solvents that are in particular water-soluble, such as $C_1$-$C_7$ alcohols; mention may in particular be made of $C_1$-$C_7$ aliphatic monoalcohols, for instance ethanol, or $C_6$-$C_7$ aromatic monoalcohols, which may be used alone or as a mixture with water.

The composition used in the process of the invention may also comprise at least one customary cosmetic ingredient, chosen in particular from propellants; oils; solid fatty substances and in particular $C_8$-$C_{40}$ esters, $C_8$-$C_{40}$ acids; $C_8$-$C_{40}$ alcohols, sunscreens; moisturizers; antidandruff agents; antioxidants; chelating agents; nacreous agents and opacifiers; plasticizers or coalescers; fillers; polymeric or non-polymeric thickeners or gelling agents other than the cellulose-based polymers already mentioned; emulsifiers; polymers, in particular conditioning or styling polymers; fragrances; silanes; crosslinking agents. The composition can, of course, comprise several cosmetic ingredients appearing in the above list.

Depending on their nature and the purpose of the composition, the normal cosmetic ingredients can be present in normal amounts which can be easily determined by those skilled in the art and which can be, for each ingredient, between 0.01% and 80% by weight. Those skilled in the art will take care to choose the ingredients included in the composition, and also the amounts thereof, such that they do not harm the properties of the compositions of the present invention.

The compositions used in the process according to the invention may be in any of the formulation forms conventionally used, and in particular in the form of an aqueous, alcoholic or aqueous-alcoholic, or oily solution or suspension; a solution or a dispersion of the lotion or serum type; an emulsion, in particular of liquid or semi-liquid consistency, of the O/W, W/O or multiple type; a suspension or emulsion of soft consistency of cream (O/W) or (W/O) type; an aqueous or anhydrous gel, or any other cosmetic form.

These compositions may be packaged in pump-action bottles or in aerosol containers, so as to apply the composition in vaporized (lacquer) form or in the form of a mousse. Such packaging forms are indicated, for example, when it is desired to obtain a spray or a mousse, for treating the hair. In these cases, the composition preferably comprises at least one propellant.

The composition which has just been described can be applied to dry or wet hair, preferably to dry hair.

The bath ratio of the applied composition may range from 0.1 to 10, more particularly from 0.2 to 5 and preferably between 0.5 and 3. The term "bath ratio" is intended to mean the ratio between the total weight of the applied composition and the total weight of keratin fibres to be treated.

As previously indicated, the step of applying the composition which has just been described is followed by a step of straightening/relaxing the keratin fibres by means of a straightening iron also known as flat tongs. The straightening iron is used at a temperature of at least 100° C., preferably at a temperature between, limits included, 100° C. and 300° C., preferably between 120° C. and 280° C., more preferably between 150° C. and 250° C. and even better still between 200 and 250° C.

The process of the invention may comprise other intermediate steps aimed at improving the straightening of the keratin fibres.

In particular, the step of applying the composition may be followed by a leave-in time. The leave-in time, namely the time of contact of the composition on the hair, is preferably at least 5 minutes, preferably between 10 and 60 minutes and preferably between 15 and 45 minutes.

Rinsing of the hair can optionally be envisaged after the application of the composition and optionally the leave-in time.

The hair may then optionally be wrung dry, preferably wrung dry.

A step of drying with a hairdryer, optionally combined with straightening with a brush (blow-drying) may be envisaged before the step of straightening using a straightening iron.

According to one particular embodiment, the straightening with the straightening iron is performed in several passes on the hair, in general 3 to 10 passes.

According to one particular embodiment, the process of the invention comprising the steps of applying the composition according to the invention to the hair, then of straightening with an iron, is carried out one or more times, optionally separated by one or more cosmetic treatments, preferably shampooing, until the desired shape or shape intensity is obtained.

The examples that follow serve to illustrate the invention without, however, being limiting in nature.

EXAMPLES

The following compositions were prepared from the ingredients indicated in the tables below, all the amounts being indicated as percent by weight of material in the given form, relative to the total weight of the composition.

|  | 1 | 2 | 3 | A (control) |
|---|---|---|---|---|
| Glycine | 10.0 (1.33M) | 5.0 (0.66M) | 2.0 (0.27M) |  |
| Sodium glycinate | 10.0 (1.03M) | 5.0 (0.51M) | 2.0 (0.2M) |  |
| Monoethanolamine |  |  |  | 1.67 (0.27M) |
| Hydrochloric acid |  |  |  | qs pH |
| Water | qs 100 | qs 100 | qs 100 | qs 100 |
| pH | 9.9 | 9.9 | 9.9 | 9.9 |
| Relaxation after 10 shampooing operations | ++++ | ++++ | +++ | -- |

++++: very strong relaxation
+++: strong relaxation
++: medium relaxation
+: a little relaxation
−: very little relaxation
−−: no relaxation Compositions 1 to 3 according to the invention and control composition A were applied to locks of dry, curly, natural caucasian hair, of 2.7 g and 20 cm long with 5 to 7 curls. After 30 minutes, the hair was dried with a hairdryer (blow-drying) and then straightened by treatment with flat tongs heated to 210° C. (10 passes per lock). The hair was then subjected to 10 shampooing operations.

For each lock, the curl relaxation was measured, namely the difference in lock length before and after treatment (including the 10 shampooing operations). It is noted that, with the process of the invention in which composition 1, 2 or 3 was applied, a strong or very strong curl relaxation is obtained after 10 shampooing operations, whereas, when control composition A is used, no relaxation is obtained.

In addition, the treated locks retain good integrity, since no breaking was observed with compositions 2 and 3 and very slight breaking, after combing, was observed with composition 1.

The process according to the invention thus makes it possible to obtain good long-lasting curl relaxation, while limiting the degradation of the hair.

The following compositions 4 to 7 according to the invention and control composition B were also applied according to the previously described protocol and the same measurements as previously were carried out.

|  | 4 | 5 | 6 | 7 | B (control) |
|---|---|---|---|---|---|
| Glycine | 3.5 (0.47M) | 2.5 (0.33M) | 5.0 (0.67M) | 2.0 (0.27M) |  |
| Sodium hydroxide at 30% AM | 3.5 (0.26M) | 1.5 (0.11M) | 5.0 (0.51M) | 2.0 (0.15M) | 2.0 (0.15M) |
| Ethanol | 10.0 |  |  |  |  |
| Methylhydroxyethyl-cellulose (STRUCTURE CEL 8000 M from Akzo Nobel) | 1.0 |  | 1.0 |  |  |
| Amodimethicone (and) Trideceth-5 (and) Trideceth-10 (BELSIL ADM LOG 1 from Wacker) | 2.0 |  |  |  |  |
| Water | qs 100 | qs 100 | qs 100 | qs 100 | qs 100 |
| pH | 9.9 | 9.6 | 9.9 | 9.9 | 13.1 |
| Relaxation after 10 shampooing operations | + | ++ | +++ | +++ | + |

It is noted that, with the process of the invention in which composition 4 was applied, a little relaxation is obtained and with compositions 5 to 7, a medium-to-strong curl relaxation is obtained. It is also noted that, at equivalent sodium hydroxide molar content, a strong curl relaxation is obtained with composition 7 which comprises glycine, whereas only a little relaxation is obtained with control composition B which does not comprise glycine.

The following composition 8 according to the invention and comparative composition C were also applied according to the previously described protocol and the same measurements as previously were carried out.

|  | 8 | C (comparative) |
|---|---|---|
| Glycine | 8.8 (1.18M) |  |
| Lysine |  | 10.0 (0.68M) |
| Sodium hydroxide at 30% AM | 8.8 (0.68M) |  |
| Guanidine hydrochloride | 5.0 (0.52M) | 5.0 (0.52M) |
| Water | qs 100 | qs 100 |
| pH | 10.1 | 10.2 |
| Relaxation after 10 shampooing operations | ++++ | + |

It is noted that, with the process of the invention in which composition 8 was applied, a significantly greater relaxation than with composition C at identical base content is obtained.

The following compositions 9 and 10 according to the invention and comparative composition D were also applied according to the previously described protocol and the same measurements as previously were carried out.

|  | 9 | 10 | D (comparative) |
|---|---|---|---|
| Alanine | 4.5 (0.5M) |  |  |
| Serine |  | 4.3 (0.5M) |  |
| Lysine |  |  | 7.3 (0.5M) |
| Sodium hydroxide at 30% AM | 4.0 (0.3M) | 4.5 (0.33M) | 3.0 (0.22M) |
| Water | qs 100 | qs 100 | qs 100 |
| pH | 10.1 | 10.0 | 11.1 |
| Relaxation after 10 shampooing operations | + | ++ | − |

It is noted that, with the process of the invention in which compositions 9 and 10 were applied, a significantly greater relaxation than with composition D at equivalent molar content of amino acid is obtained.

Finally, the following compositions 11 to 15 according to the invention and comparative composition E were also applied according to the previously described protocol and the same measurements as previously were carried out.

|  | 11 | 12 | 13 | 14 | 15 | E (comparative) |
|---|---|---|---|---|---|---|
| Glycine | 3.5 (0.47M) | 3.5 (0.47M) | 3.5 (0.47M) | 3.5% (0.47M) | 2.1 (0.28M) | |
| Sodium hydroxide at 30% AM | 3.5 (0.26M) | 3.5 (0.26M) | 3.5 (0.26M) | 3.5% (0.26M) | 2.1 (0.16M) | |
| Monoethanolamine | | | | | | 1.0 (0.16M) |
| Ethanol | 10 | 10.0 | 10 | 10% | | |
| Urea | 5.0 (0.83M) | 10.0 (1.66M) | | | 15.0 (2.58M) | 15.0 (2.58M) |
| Hydroxyethylurea | | | 21.8 (0.83M) | 6.3 (0.24M) | | |
| Amodimethicone (and) Trideceth-5 (and) Trideceth-10 (BELSIL ADM LOG 1 from Wacker) | 2.0 | 2.0 | 2.0 | 2.0 | | |
| Methylhydroxy-ethylcellulose (STRUCTURE CEL 8000M from Akzo Nobel) | 1.0 | 1.0 | 1.0 | 1.0 | | |
| Water | qs 100 | qs 100 | qs 100 | qs 100 | qs 100 | qs 100 |
| pH | 9.9 | 9.9 | 9.9 | 9.9 | 10.0 | 11.9 |
| Relaxation after 10 shampooing operations | +++ | +++ | ++++ | ++++ | ++++ | ++ |

It is noted that, with the process of the invention in which compositions 11 to 15 were applied, a strong to very strong curl relaxation is obtained. It is also noted that, with composition 15, a significantly greater relaxation than with composition E is obtained, at identical base content, and this with a pH of composition 15 according to the invention which is lower than that of comparative composition E.

The invention claimed is:

1. A method for treating keratin fibers, comprising:
   a) applying to the keratin fibers a composition, the composition comprising:
      at least one amino acid chosen from those according to formulae (I) and (II) below, the betaine forms thereof, the optical isomers thereof, the solvates thereof, or the organic or inorganic base or acid salts thereof:

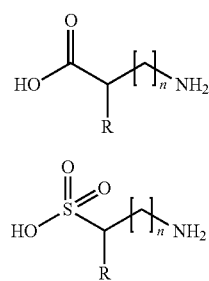

wherein:
   R is chosen from hydrogen or a linear or branched, $C_1$-$C_5$ alkyl group, optionally substituted with at least one group chosen from hydroxyl, —C(O)—OH, —S(O)$_2$—OH, —C(O)—O$^-$, M$^+$, or —S(O)$_2$—O—, wherein M$^+$ is a cationic counterion, and
   n is equal to 0 or 1,
wherein the pH of the composition is greater than or equal to 8, at a temperature of 25° C.; and
   b) straightening/relaxing the keratin fibers by means of a straightening iron at a temperature of at least 100° C.

2. The method according to claim 1, wherein the composition further comprises at least one basifying agent or at least one acidifying agent.

3. The method according to claim 2, wherein the at least one basifying agent is chosen from sodium hydroxide, potassium hydroxide, lithium hydroxide, calcium hydroxide, or magnesium hydroxide.

4. The method according to claim 2, wherein the at least one basifying agent is chosen from the conjugated bases of the amino acids of formulae (I) or (II) according to formulae (Ib) and (IIb), below:

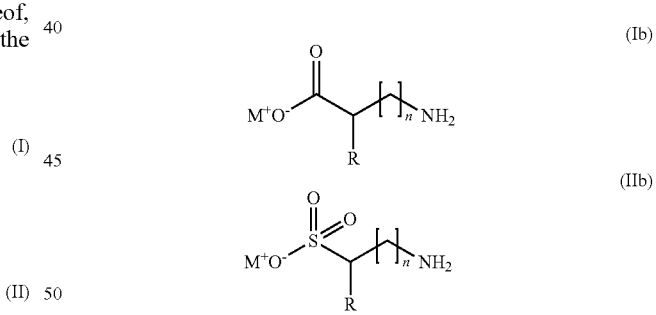

wherein:
   R is chosen from hydrogen or a linear or branched, $C_1$-$C_5$ alkyl group, optionally substituted with at least one group chosen from hydroxyl, —C(O)—OH, —S(O)$_2$—OH, —C(O)—O$^-$, M$^+$, or —S(O)$_2$—O$^-$,
   M$^+$ is a cationic counterion, and
   n is equal to 0 or 1.

5. The method according to claim 2, wherein the at least one acidifying agent is chosen from an inorganic acid or an organic acid.

6. The method according to claim 2, wherein the at least one acidifying agent is chosen from hydrochloric acid, orthophosphoric acid, sulfuric acid, citric acid, lactic acid, glycolic acid, gluconic acid, tartaric acid, or malic acid.

7. The method according to claim 1, wherein the at least one amino acid is chosen from the amino acids according to formula (I), the betaine forms thereof, the optical isomers thereof, the solvates thereof, or the organic or inorganic base or acid salts thereof.

8. The method according to claim 1, wherein the composition comprises:
   the at least one amino acid chosen from those according to formulae (I) and (II), and
   at least one basifying agent chosen from the conjugated base of the at least one amino acid according to formulae (Ib) or (IIb) below:

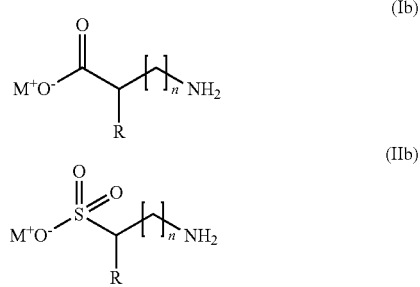

wherein:
   R is chosen from hydrogen or a linear or branched, $C_1$-$C_5$ alkyl group, optionally substituted with at least one group chosen from hydroxyl, —C(O)—OH, —S(O)$_2$—OH, —C(O)—O$^-$, M$^+$, or —S(O)$_2$—O$^-$,
   M$^+$ is a cationic counterion, and
   n is equal to 0 or 1.

9. The method according to claim 8, wherein the molar ratio of the at least one amino acid according to formulae (I) or (II) to its conjugated base according to formulae (Ib) or (IIb) ranges from about 1 to about 100.

10. The method according to claim 1, wherein the at least one amino acid is neutral or acidic.

11. The method according to claim 1, wherein the at least one amino acid is chosen from glycine, alanine, serine, beta-alanine and taurine, or the salts thereof.

12. The method according to claim 1, wherein the at least one amino acid is present in the composition in an amount ranging from about 1.5% to about 15% by weight, relative to the total weight of the composition.

13. The method according to claim 1, wherein the pH of the composition is less than two units from the pKa of the equilibrium of the at least one amino acid of formula (I) or (II) with its conjugated base (Ib) or (IIb).

14. The method according to claim 1, wherein the pH of the composition ranges from 8 to 12.

15. The method according to claim 1, wherein the composition further comprises at least one amino denaturing agent.

16. The method according to claim 1, wherein the composition further comprises at least one thickener.

17. The method according to claim 1, wherein the composition further comprises at least one additional ingredient chosen from non-ionic surfactants or silicones.

18. The method according to claim 1, wherein the straightening/relaxing step is carried out by means of a straightening iron at a temperature ranging from about 100° C. to about 300° C.

19. The method according to claim 1, wherein the straightening/relaxing step is carried out by means of a straightening iron at a temperature ranging from about 150° C. to about 250° C.

* * * * *